United States Patent [19]

Naylor

[11] Patent Number: 4,680,269
[45] Date of Patent: Jul. 14, 1987

[54] METHOD AND APPARATUS FOR PREVENTING CROSS-CONTAMINATION OF BIOCHEMICAL TEST WELLS IN A MICROTITER TEST PLATE

[75] Inventor: Harry B. Naylor, Lakewood, Colo.

[73] Assignee: Pasco Laboratories, Inc., Wheatridge, Colo.

[21] Appl. No.: 723,360

[22] Filed: Apr. 15, 1985

[51] Int. Cl.⁴ .............................................. C12M 1/20
[52] U.S. Cl. .................................... 435/301; 423/237
[58] Field of Search ................................... 435/30–32, 435/287, 297–301, 810; 422/56, 61, 102, 101; 55/524; 423/237, 238

[56] References Cited

U.S. PATENT DOCUMENTS

| | | | |
|---|---|---|---|
| 3,438,737 | 4/1969 | Atkinson et al. | 422/56 |
| 3,873,269 | 3/1975 | Kraffczyk et al. | 422/56 |
| 4,070,300 | 1/1978 | Moroni et al. | 423/237 |
| 4,080,423 | 3/1978 | Smith et al. | 423/238 |

*Primary Examiner*—Samuel Scott
*Assistant Examiner*—Noah Kamen
*Attorney, Agent, or Firm*—Edwin L. Spangler, Jr.

[57] ABSTRACT

This invention relates to a porous barrier impregnated with an acidic compound positioned in overlying relation atop the biochemical test wells portion of an antibiotic microtiter test plate effective to intercept and neutralize volatile alkaline products evolved through bacterial growth taking place therein before they can diffuse and contaminate nearby test wells and produce erroneous pH-sensitive color tests. The invention also relates to an improved method for preventing cross-contamination of the biochemical tests being carried out in test wells adjacent microtiter test wells, the contents of which are being analyzed for antibacterial activity, which consists of covering the biochemical test wells with a porous medium impregnated with an acidic compound capable of neutralizing gaseous alkaline products resulting from bacterial growth in wells containing sub-inhibitory antibiotic levels thereby protecting the biochemical tests from erroneous pH-sensitive indicator color changes.

5 Claims, 3 Drawing Figures

METHOD AND APPARATUS FOR PREVENTING CROSS-CONTAMINATION OF BIOCHEMICAL TEST WELLS IN A MICROTITER TEST PLATE

The traditional methodology employed to determine the antimicrobial activity of certain antibiotics which utilized a plurality of individual test tubes in which cultures of the infectious organism were propagated and nourished preparatory to being inoculated with varying concentrations of the compound whose efficacy was being investigated has long ago given way to faster, more efficient and much more accurate modern techniques. Among these is a "microtiter test plate" designed to simultaneously determine both the minimum inhibitory concentration of one or more antibiotics capable of killing the infectious organism along with its identity. The "microtiter test plate" consists of a plurality of miniature test wells formed integral with one another on a common substrate. At a manufacturing facility especially equipped to mass produce these test plates, hundreds of them are prepared in which minute quantities of many different antibiotics or so-called "antimicrobials" at known incrementally-increasing concentrations are placed in most of the wells. A relatively small number of test wells, usually grouped together in a given area of the test plate, are reserved for special growth media and referred to as "biochemical test wells." A different medium is placed in each biochemical test well, and each medium is designed to determine a specific biochemical reaction produced during growth of an infectious agent introduced therein. After the wells are filled, the plates and their contents are frozen. The frozen plates, together with certain auxiliary equipment, are then delivered to a facility, be it a hospital, commercial laboratory, or physician's office where tests are to be conducted. Just prior to use, the plates and their contents are allowed to thaw before being inoculated. Using a special device, minute but uniform concentrations of a growing culture of the infectious organism in question are simultaneously introduced into each test well of the "microtiter test plate". Many of the media designed for biochemical testing contain color indicators such as, for example, brom thymol blue, phenol red, or brom cresol purple, all of which are pH-sensitive and respond to minute changes in pH by changing hue. After incubation of the plate, color changes of the indicators are observed and recorded. The results, along with those of other biochemical tests not involving pH changes, are used to identify the infectious organism. The antibiotic test results are determined by observing for growth as evidenced by turbidity or cell sediment in wells where growth has occurred or, alternatively, the lack of it where growth was prevented by the antibiotic. Reading of the test plate can be done visually, however, in more sophisticated procedures computerized analysis of the test plates is carried out rapidly and with a good deal more accuracy than is possible by visual inspection. A successful test, obviously, tells the attending physician the identity of the infectious organism, the antibiotic(s) which will kill it, and the dosage level(s) required to do so.

Unfortunately, use of "microtiter test plates" designed to measure both antibiotic susceptibility and biochemical reactions of an infectious organism simultaneously on a single plate can cause erroneous biochemical test results to occur. It has become apparent to investigators using these test plates that false negative tests for various fermentation and oxidation reactions have occurred as indicated by a rise in pH when it should go down as a result of acid production. False positive tests for decarboxylase activity have also been observed. The cause of these erroneous biochemical test results is primarily, the evolution of volatile alkaline material, more specifically ammonia ($NH_3$), by the microorganisms growing in the surrounding test wells. This was not a problem when the cultures were grown in individual stoppered or cotton-plugged test tubes; however, using the aforementioned modern techniques, the volatile alkaline products generated in connection with the bacterial growth in one or more of the individual test cells invade the common atmosphere thereabove and contaminates those nearby thus causing the erroneous readings.

The prior art attempts at solving this perplexing problem have, so far as applicant is aware, taken the form of taping a gas-impervious cover of some sort over the test wells. This approach has proven to be messy, tedious and, most significant, still subject to producing erroneous results under certain circumstances. It has now been discovered, however, that a simple and effective cure for the problem of cross-contamination does, in fact, exist which consists of the novel, yet unobvious, expedient of covering the wells of the microtiter plate subject to the generation of volatile alkaline products with a porous barrier impregnated with a compound effective to absorb and neutralize the products thus evolved before they can reach and contaminate the processes taking place in the wells nearby.

Others before applicant have covered the wells in their microtiter plates with either porous or non-porous membranes of one type or another such as, for example, those disclosed in U.S. Pat. Nos. 2,561,339; 3,540,857; 3,540,858; 3,888,770; 4,154,795; 4,198,484; 4,304.865; and 4,317,726. While some of these covers for the individual wells have as one of their functions the prevention of cross-contamination, many of the others are primarily filters and only incidentally inhibit contamination from nearby wells. Other approaches to the cross-contamination problem have taken the form of upstanding walls or ribs separating groups of wells as disclosed in U.S. Pat. No. 3,826,717 or, alternatively, using a solidifiable liquid culture medium as taught by Haque et al in their U.S. Pat. No. 4,042,463. There are other U.S. patents known to applicant which relate to microbial test kits of various types; however, they do not appear to address the problem of cross-contamination prevention other than generally by keeping the cultures separate in their own individual wells.

Despite the considerable amount of prior art activity directed at preventing cross-contamination through the use of some sort of barrier covering the individual wells, no one insofar as applicant is aware has impregnated their barrier with a substance which will interact with the evolved contaminants to neutralize same such that, even if they should reach a nearby well, they will have been rendered ineffectual to alter the results.

It is, therefore, the principal object of the present invention to provide a novel and improved multiple-well antimicrobial test kit which includes a cross-contamination barrier effective to intercept and neutralize any alkaline gaseous contaminants evolved.

A second objective of the invention herein disclosed and claimed is the provision of a method for preventing cross-contamination of nearby test wells in a biological activity test kit wherein a porous membrane is impregnated with an acidic compound effective to neutralize ammonia and then placed in a position to intercept and neutralize any of the latter gas that may be evolved in one well before it can reach and contaminate those nearby.

Another object of the within-described invention is that of providing a simple, yet very effective, solution to a vexing contamination problem.

Still another objective of the invention forming the subject matter hereof is to provide an antimicrobial test kit wherein the empty wells of one multiple-well test plate cooperate with the acid-impregnated membrane to hold the latter down in essentially sealed relation over the inoculated wells of a second test plate when the first is used as a lid.

Further objects of the invention are to provide an ammonia-absorptive barrier for antimicrobial test kits which is inexpensive yet effective, easy to use, versatile, and which requires no modification whatsoever in the existing units.

Other objects will be in part apparent and in part pointed out specifically hereinafter in connection with the description of the drawings that follow, and in which.

Figure 1:
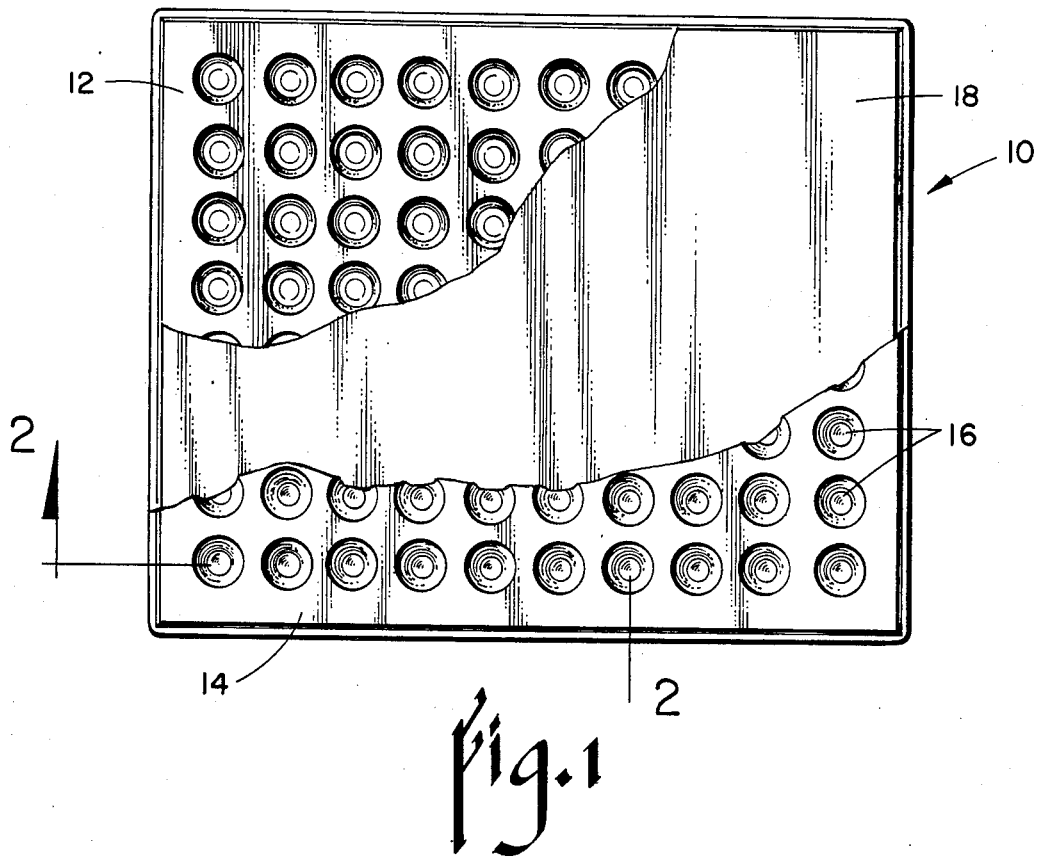
FIG. 1 is a top plan view of the microtiter test plate with the impregnated gas barrier in place on top thereof and the lid covering both, portions of each of the aforementioned elements having been broken away to expose the one thereunder.
Figure 2:
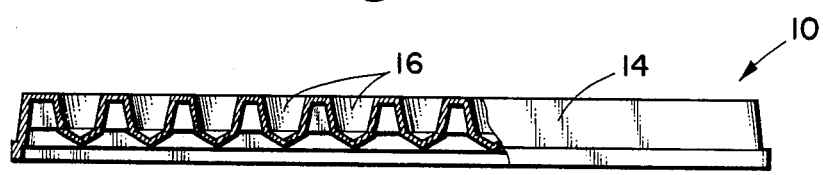
FIG. 2 is an exploded section taken along line 2—2 of FIG. 1.
Figure 2:
Figure 2:
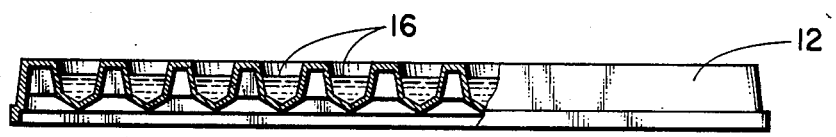
Figure 2:

Referring next to the drawings for a detailed description of the present invention, reference numeral 10 has been selected to broadly designate the antimicrobial test kit in its entirety while numerals 12 and 14 have been chosen to similarly denote its plate and lid, respectively. Actually, in the particular form illustrated, the plate and lid are identical and, therefore, interchangeable were it not for the fact that the several wells 16 contained in the plate are, of course, ordinarily prefilled with serial concentrations of several different antibiotics or antimicrobics and frozen preparatory to delivering same to the user. There are several different antimicrobial tests and only certain antimicrobics respond to these tests, therefore, the test plates differ in which of the antimicrobics they contain although certain ones like, for example, ampicillin, cephalothin and piperacillin may be common to more than one. The concentrations of the antimicrobic in each well of the series generally double from one to the next over the full range of clinical interest.

One special type of micro test plate designed to determine the identity of the pathogenic organism and its antibiotic sensitivity pattern simultaneously includes a section set aside and reserved for special media formulated to measure various biochemical reactions produced during growth of the pathogenic organism. It is in this biochemical test area of the plate that the cross-contamination problem caused by volatile alkaline compounds such as ammonia is critical. Consequently, it is imperative that these biochemical test wells be protected from the volatile alkaline products in the confined atmosphere above the wells whether these products are produced in the biochemical test wells or in the surrounding antibiotic test wells. Accordingly, while FIG. 1 shows the barrier which has been indicated in a general way by numeral 18 as covering all the wells 16 of the test plate 12, in actual use its coverage can be confined to just those wells containing biochemicals.

The barrier 18 in the particular form tested comprised sheets of commercially-available filter paper (Whatman) which were dipped in the alkaline-gas absorptive solutions being tested preparatory to being blotted, dried and pressed flat. Once dry, the barriers thus impregnated were placed atop the test wells in the microtiter test plates 12 all of which had been filled with Mueller-Hinton broth and inoculated with *Pseudomonas aeruginosa* which was selected as the test organism because of its ability to produce maximum protein degradation thereby resulting in substantial ammonia production. These plates were then covered with lids 14 and incubated for a period of eighteen hours.

Figure 3:
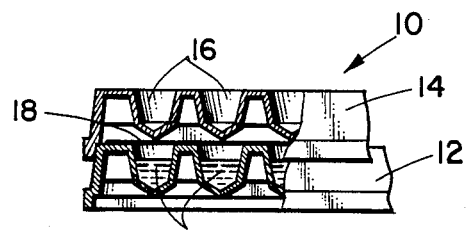
FIG. 3 is a section like FIG. 2 and to the same scale but showing the elements in assembled gas-neutralizing relation.
Figure 3:

The bottoms 20 of the wells 16 in the lids 14 function as shown in FIG. 3 with the latter in place upon the plate 12 to hold the barrier 18 down snugly atop the inoculated wells in the latter thus insuring that no gas can migrate from one to another underneath the barrier but instead must come into intimate contact therewith and with its ammonia-neutralizing impregnate. While, obviously, if left undisturbed and preferably covered in some fashion, the barrier will remain effective to trap and neutralize most, if not all, of the evolved alkaline gases; nevertheless, the "hold-down" function of the lid wells is considered to be an important safeguard.

Since the purpose of the test was to determine, if possible, the effectiveness of the impregnated barriers and not to kill the growing organism, there was no need to include any antimicrobic agent. It was necessary, however, to test the paper barrier itself without any impregnate to determine its ammonia-nitrogen concentration thus establishing a background level control. In addition, barriers impregnated with solutions of various concentrations of the ammonia-absorptive agent were prepared for analysis to determine the level of retained agent in each case, as well as the amount of ammonia nitrogen present before exposure of the barriers to the inoculated microtiter test plates.

Table I which follows shows the results of the test on the unexposed barriers impregnated with solutions of different concentrations of potassium dihydrogen phosphate ($KH_2PO_4$) as the ammonia-absorptive agent.

TABLE I

| Sample No. | % $KH_2PO_4$ in impregnating solution | Mg. $KH_2PO_4$ retained in barrier | Mg. $NH_3$—N in barrier |
|---|---|---|---|
| 1 | 0 | 13 | 0.13 |
| 3 | 5 | 90 | 0.36 |
| 4 | 10 | 145 | 0.28 |
| 2 | 15 | 320 | 0.26 |

The data recorded in the above Table I shows that the untreated barrier has a low level of 0.13 mg. of ammonia-nitrogen ($NH_3$—N) and that the level increases to an average of 0.30 mg. $NH_3$—N upon treatment with $KH_2PO_4$ solutions of 5%, 10% and 15% concentrations.

The data presented in Table II resulted from analyses made on three barriers impregnated with a 5% $KH_2PO_4$ solution, three barriers impregnated with a 10% $KH_2PO_4$ solution and one barrier impregnated with a 15% $KH_2PO_4$ solution prior to being exposed to the ammonia being evolved by the *Pseudomonas aeruginosa* culture being propogated in the test wells.

TABLE II

| Sample No. | % KH$_2$PO$_4$ in impregnating solution | Mg. KH$_2$PO$_4$ retained in barrier | Mg. NH$_3$—N in barrier |
|---|---|---|---|
| 5 | 15 | 320 | 3.8 |
| 6-1 | 5 | | 3.1 |
| 6-2 | 5 | 87* | 3.7 |
| 6-3 | 5 | | 3.5 |
| 7-1 | 10 | | 3.1 |
| 7-2 | 10 | 150* | 4.1 |
| 7-3 | 10 | | 4.6 |

*only one barrier of the three tested

Table II reveals an average of 3.4 mg. of ammonia nitrogen retained in the barriers impregnated with a 5% KH$_2$PO$_4$ solution while the average weight rose to about 3.9 mg. in the barriers impregnated with a 10% KH$_2$PO$_4$ solution. This translates into a capacity to absorb and neutralize the ammonia of approximately 0.64 meq. of KH$_2$PO$_4$ in the 5% samples and about 1.1 meq. in the 10% ones. Of the average of 3.4 mg. of ammonia-nitrogen absorbed by the KH$_2$PO$_4$ impregnate in the 5% samples, this amounts to only some 37.5% of its total absorptive capacity being used. Similarly, the average of 3.9 mg. of ammonia-nitrogen absorbed by the KH$_2$PO$_4$ in the 10% samples used up only some 26% of the somewhat greater absorptive capacity of the latter. One can conclude, therefore, that treatment of the paper with a 15% solution of the ammonia-absorptive agent in the form of potassium dihydrogen phosphate results in a barrier which is far more than adequate to neutralize the alkaline gases evolved from Mueller-Hinton broth by an organism such as *Pseudomonas aeruginosa* which is known to possess a strong protein degradation potential. Even treatment with a 5% solution yielded barriers which proved to have ample capacity to handle and neutralize the ammonia evolved from those cultures totally uninhibited by any antimicrobic agent. Nevertheless, since a significant safety factor is advisable, a 5% concentration would appear to approximate a wise lower limit for impregnating solutions although, obviously, concentrations of almost two-thirds less could, conceivably, still handle the evolved ammonia without exhausting its capacity to do so.

What is claimed is:

1. In combination in a test kit for use in evaluating the effectiveness of antibacterial agents to kill pathogenic bacteria, which comprises: a base having a plurality of upwardly-opening wells, a lid fitted to the base and having a cover-forming portion spaced above the wells therein cooperating therewith to confine and define a common atmosphere above the wells, and a porous sheet impregnated with an acidic compound effective to intercept and neutralize alkaline gases evolved in the wells therebeneath when positioned to cover said wells, said lid including means projecting from the underside of said cover-forming portion positioned and adapted to engage said sheet and hold same in substantially sealed relation atop the wells in the base.

2. The improved method for preventing cross-contamination of bacterial test wells in a multiple-well antimicrobial test plate wherein certain of the wells contain growing cultures of bacteria of the type that evolve alkaline gases, which comprises: covering the wells with a porous membrane impregnated with an acidic compound effective to intercept and neutralize said evolved gases.

3. The improved method as set forth in claim 2 in which: the membrane is impregnated with potassium dihydrogen phosphate.

4. The improved method as set forth in claim 2 in which: the mole equivalents of the potassium dihydrogen phosphate substantially exceeds the mole equivalents of the evolved gases.

5. The improved method as set forth in claim 2 in which: the concentration of the potassium dihydrogen phosphate in the solutions used to impregnate the porous membranes is between approximately 5% and 15%.

* * * * *